United States Patent
McKay

(10) Patent No.: US 8,486,080 B2
(45) Date of Patent: Jul. 16, 2013

(54) BONE REPLACEMENT MATERIAL DELIVERY DEVICES AND METHODS OF MONITORING BONE REPLACEMENT MATERIAL

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 294 days.

(21) Appl. No.: 12/842,082

(22) Filed: Jul. 23, 2010

(65) Prior Publication Data
US 2012/0022541 A1 Jan. 26, 2012

(51) Int. Cl.
*A61B 17/58* (2006.01)
(52) U.S. Cl.
USPC ........................................................ 606/94
(58) Field of Classification Search
USPC ..................................................... 606/92–94
See application file for complete search history.

(56) References Cited

U.S. PATENT DOCUMENTS

| | | | |
|---|---|---|---|
| 5,951,563 A | 9/1999 | Brown | |
| 6,086,594 A | 7/2000 | Brown | |
| 6,884,264 B2 | 4/2005 | Spiegelberg et al. | |
| 7,144,398 B2 | 12/2006 | Chern Lin et al. | |
| 7,559,932 B2 | 7/2009 | Truckai et al. | |
| 7,632,294 B2 | 12/2009 | Milbodker et al. | |
| 7,981,381 B2 * | 7/2011 | Lurvey et al. | 422/400 |
| 2001/0004710 A1 | 6/2001 | Felt et al. | |
| 2004/0013839 A1* | 1/2004 | Ko et al. | 428/40.1 |
| 2006/0089655 A1 | 4/2006 | Watkins et al. | |
| 2007/0092451 A1* | 4/2007 | Loveridge et al. | 424/10.1 |
| 2007/0118144 A1 | 5/2007 | Truckai et al. | |
| 2007/0154874 A1 | 7/2007 | Sherman et al. | |
| 2007/0191858 A1* | 8/2007 | Truckai et al. | 606/92 |
| 2007/0233147 A1 | 10/2007 | Vendrely et al. | |
| 2007/0287989 A1* | 12/2007 | Crawford et al. | 604/507 |
| 2008/0027455 A1 | 1/2008 | Boudeville et al. | |
| 2008/0086142 A1 | 4/2008 | Kohm et al. | |
| 2008/0091207 A1 | 4/2008 | Truckai et al. | |

(Continued)

FOREIGN PATENT DOCUMENTS

WO 2008146021 A1 12/2008

OTHER PUBLICATIONS

International Search Report and Written Opinion for PCT/US2011/044072, the counterpart application mailed on Mar. 19, 2012.

*Primary Examiner* — Kevin T Truong
*Assistant Examiner* — Christopher Beccia
(74) *Attorney, Agent, or Firm* — Sorell Lenna & Schmidt LLP

(57) ABSTRACT

Bone material delivery devices and methods of using the devices are provided. The bone material delivery devices and methods comprise thermochromic material disposed on the exterior of the syringe, the thermochromic material configured to provide an indication of temperature, viscosity, and/or age of bone replacement material in the interior of the syringe. In some embodiments, a time indicating label is disposed on the exterior of the syringe, the time indicating label comprising a label substrate having a first surface comprising an acid-base indicator and a second surface comprising an activator, wherein when the first surface is brought into contact with the second surface or when the second surface is brought into contact with the first surface, at least a portion of the label changes color indicating elapsed time. In some embodiments, the devices and methods allow the practitioner to know the dough time, working time, and setting time of the bone replacement material when it is in the syringe.

17 Claims, 4 Drawing Sheets

U.S. PATENT DOCUMENTS

| | | |
|---|---|---|
| 2008/0154273 A1 | 6/2008 | Shadduck et al. |
| 2008/0255570 A1 | 10/2008 | Truckai et al. |
| 2009/0062808 A1 | 3/2009 | Wolf, II |
| 2009/0076518 A1 | 3/2009 | Bowman et al. |
| 2009/0084978 A1 | 4/2009 | Chandler et al. |
| 2009/0093818 A1 | 4/2009 | Baroud |
| 2009/0149878 A1 | 6/2009 | Truckai et al. |
| 2009/0187192 A1 | 7/2009 | Rabiner et al. |
| 2009/0198242 A1 | 8/2009 | Truckai et al. |
| 2009/0303440 A1* | 12/2009 | Heacock et al. ............... 351/219 |
| 2009/0305430 A1 | 12/2009 | Chandler |
| 2009/0306674 A1* | 12/2009 | Chandler ........................ 606/93 |
| 2010/0016467 A1 | 1/2010 | Truckai et al. |
| 2010/0030220 A1 | 2/2010 | Truckai et al. |
| 2010/0087827 A1 | 4/2010 | Baroud |
| 2010/0091606 A1 | 4/2010 | Kwan et al. |
| 2010/0110436 A1 | 5/2010 | Chandler et al. |
| 2011/0054481 A1* | 3/2011 | Sproul ........................... 606/94 |

* cited by examiner

BONE REPLACEMENT MATERIAL DELIVERY DEVICES AND METHODS OF MONITORING BONE REPLACEMENT MATERIAL

BACKGROUND

Bone replacement material, such as bone cements, can be used during certain medical treatments to help repair and/or reconstruct bone (e.g., fractured bone). The ability of certain bone replacement material to repair and/or reconstruct bone can be enhanced by the inclusion of bioactive agents (e.g., bone morphogenic protein), which promote the growth of bone.

To prepare bone replacement material, a powdery substance is generally combined with a liquid, and the resultant combination is mixed together and begins the curing process to form a bone replacement material dough or paste. The bone replacement material dough or paste can then be delivered to a treatment site (e.g., a fracture site) to help repair and/or reconstruct the bone.

The bone replacement material should be allowed to cure for a time so that the material is not too fluid, facilitates handling of the material and minimizes the risk of the material flowing undesirably outside the area of implantation. However, if the bone replacement material is allowed to cure too long before delivery, the bone replacement material will be too thick or even harden causing difficulties in working with or setting the bone cement. If left in the delivery device too long, the bone replacement material may completely harden rendering it useless.

Often the practitioner will determine the extent of cure of the bone replacement material by feel, involving kneading the bone replacement material as it cures and relying on judgment to assess properties of the bone replacement material such as viscosity (or firmness), tackiness, and smoothness (grittiness) before it is delivered to the implantation site. Assessment of these properties can be affected by environmental conditions, such as temperature and humidity.

Relying on subjective techniques such as feel to determine the extent of cure has the disadvantage that it is not always reliable, and it can be difficult to train new users of these techniques. Furthermore, the curing time of bone replacement material can be affected by variations in environmental conditions, such as humidity and temperature. Variations in the temperature of the practitioner's fingers as he kneads a sample of a bone cement can lead to variations in the extent of cure of that sample, relative to the extent of cure of the remainder of the cement which is to be used in the procedure. Also, variations in temperature and humidity will affect the perception of the tackiness of the cement.

Therefore, there is a need for bone replacement material delivery devices and methods that facilitate delivery of bone replacement material by allowing the user to more reliably monitor the cure of bone replacement material and reduce the need for the practitioner to rely on subjective techniques to monitor the cure of the bone replacement material.

SUMMARY

Methods and bone replacement material delivery devices are provided that increase the efficiency of delivery of bone replacement material by allowing the user to more reliably monitor the cure of bone replacement material. The methods and bone replacement material delivery devices provided take the guess work out of determining the cure state of the bone replacement material and reduce the need for the practitioner to rely solely on subjective techniques to monitor the cure of the bone replacement material.

In one embodiment, there is a bone replacement material delivery device, comprising: a syringe having an exterior, and an interior configured to receive bone replacement material, the syringe comprising a plunger slidable within the interior of the syringe, the plunger having a first end and a second end, the second end configured for moving the first end of the plunger to at least a depressed position to displace bone replacement material from the syringe at the appropriate time; and a thermochromic material disposed in or on the exterior of the syringe, the thermochromic material configured to provide an indication of temperature, viscosity, and/or age of bone replacement material in the interior of the syringe.

In another embodiment, there is a bone replacement material delivery device, comprising: a syringe having an exterior, and an interior configured to receive bone replacement material, the syringe comprising a plunger slidable within the interior of the syringe, the plunger having a first end and a second end, the second end configured for moving the first end of the plunger to at least a depressed position to displace any bone replacement material from the syringe at the appropriate time; and a time indicating label disposed on the exterior of the syringe, the time indicating label having a first surface comprising an acid-base indicator and a second surface comprising an activator, wherein when the first surface is brought into contact with the second surface or when the second surface is brought into contact with the first surface, at least a portion of the label changes color indicating elapsed time.

In yet another embodiment, there is a method of monitoring curing of mixed bone replacement material, the method comprising providing a syringe having an exterior, and an interior having mixed bone replacement material therein, the syringe comprising a plunger slidable within the interior of the syringe, the plunger having a first end and a second end, the second end configured for moving the first end of the plunger to at least a depressed position to displace mixed bone replacement material from the syringe at the appropriate time; and monitoring (i) a thermochromic material disposed in or on the exterior of the syringe, the thermochromic material configured to provide an indication of temperature, viscosity, and/or age of bone replacement material in the interior of the syringe or (ii) a time indicating label disposed on the exterior of the syringe, the time indicating label comprising a label having a first surface comprising an acid-base indicator and a second surface comprising an activator, wherein when the first surface is brought into contact with the second surface or when the second surface is brought into contact with the first surface, at least a portion of the label changes color indicating elapsed time, thereby monitoring the curing of mixed bone replacement material.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
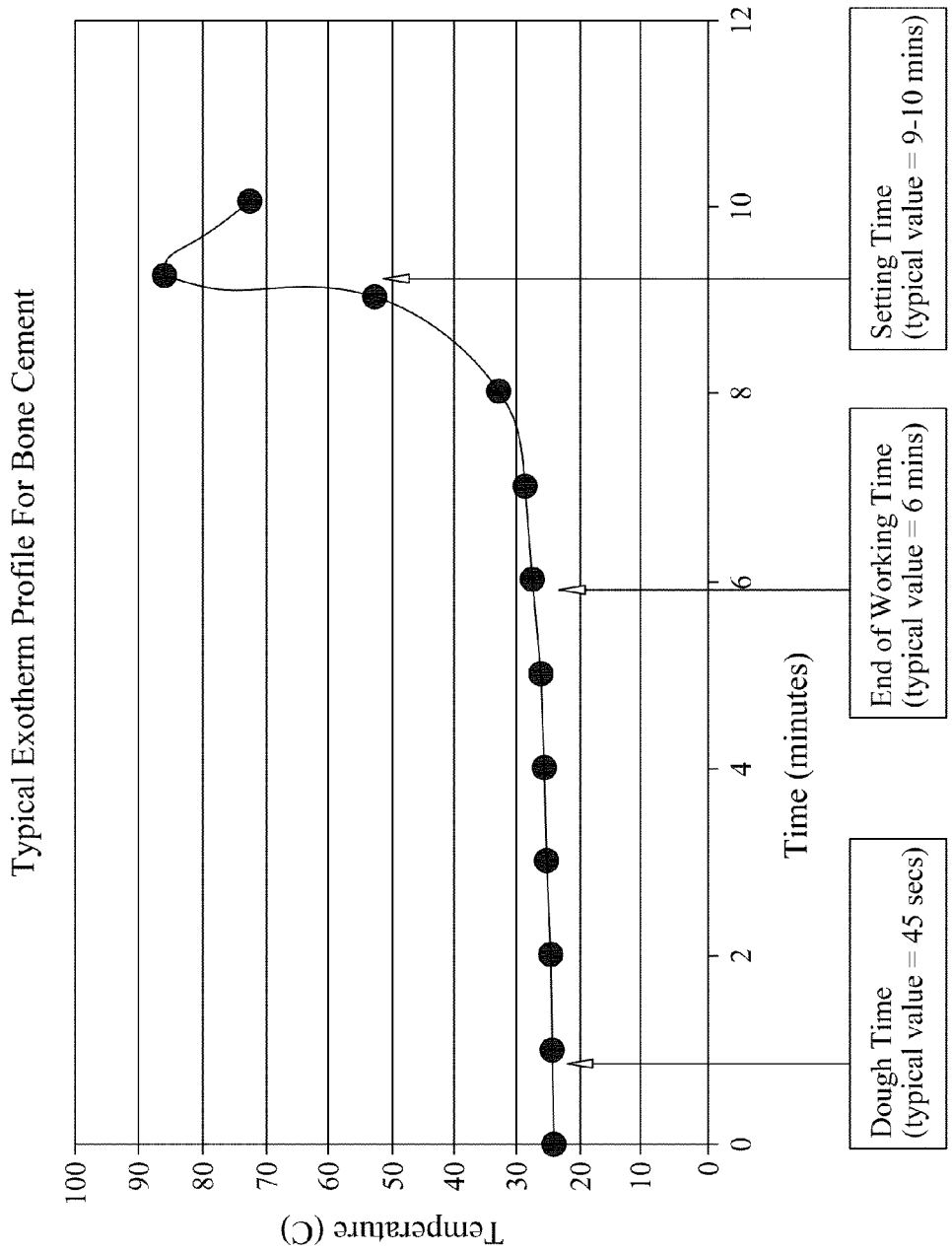
FIG. 1 is graphic illustration showing the various phases of typical bone replacement material and its approximate time and temperature.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. Thus, for example, reference to "a thermochromic material" includes one, two, three or more thermochromic materials.

The term "practitioner" or "user" means a person who is using the methods and/or devices of the current disclosure on the patient. This term includes, without limitation, doctors (e.g., surgeons, interventional specialists, physicians), nurses, nurse practitioners, other medical personnel, clinicians, veterinarians, or scientists.

The term "mammal" refers to organisms from the taxonomy class "mammalian," including but not limited to humans, other primates such as chimpanzees, apes, orangutans and monkeys, rats, mice, cats, dogs, pigs, cows, horses, etc. In various embodiments, the mammal is a human patient.

The term "implantable" as utilized herein refers to a device (e.g., bone cement, bone replacement material, etc.) retaining potential for successful placement within a mammal.

Treating or treatment of a disease or condition refers to executing a protocol, which may include the use of the devices and methods herein and/or administering one or more bone materials to a patient (human, normal or otherwise, or other mammal), in an effort to diagnose and alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient.

The term "transparent" refers to a layer through which, thermochromic material, color, ink or printing may be seen.

The term "thermochromic" is the ability of substance to change color due to a change in temperature.

Delivery Devices

Methods and bone replacement material delivery devices are provided that increase the efficiency of delivery of bone replacement material by allowing the user to more reliably monitor the cure of bone replacement material. The methods and bone replacement material delivery devices provided take the guess work out of determining the cure state of the bone replacement material and reduce the need for the practitioner to rely solely on subjective techniques to monitor the cure of the bone replacement material.

In one embodiment, there is a bone replacement material delivery device, comprising: a syringe having an exterior, and an interior configured to receive bone replacement material, the syringe comprising a plunger slidable within the interior of the syringe, the plunger having a first end and a second end, the second end configured for moving the first end of the plunger to at least a depressed position to displace any bone replacement material from the syringe; and a thermochromic material disposed in or on the exterior of the syringe, the thermochromic material configured to provide an indication of temperature, viscosity, and/or age of any bone replacement material in the interior of the syringe.

Referring to FIG. 1, it is graphic illustration showing the various phases of bone replacement material in the prior art and its approximate time and temperature. In this illustration, the exotherm profile and curing time is shown for prior art bone replacement material for SmartSet GVH® available from Depuy International Limited.

Bone replacement material curing is often divided into three phases. The mixing phase is the first phase in which monomer is mixed with powder and the result is a sticky, runny paste. In the mixing phase, the components of the bone replacement material react and typically there is polymerization of the acrylate monomer and copolymerization with the acrylate polymer particles. This type of reaction is exothermic and causes an increase in temperature. When the cement is no longer runny and sticky, a dough or paste will appear and this is often referred to dough time or time to dough, which is the time from initial mix to the time the bone replacement material is no longer sticky. In FIG. 1, the components of the bone replacement material were stored at 23° C. before being mixed. After mixing the time of appearance of a doughy or paste state for the bone replacement material was 45 seconds (indicated as dough time).

The second phase in the cure is the working phase where the bone replacement material is now in a dough-like or paste-like state and is not sticky. The practitioner has time to work with the bone replacement material and implant it at the desired site. In FIG. 1, the temperature of the bone replacement material increased slowly over an initial period of about 6 minutes. The practitioner has time to work with the bone replacement material referred to as working time, which ends in about 6 minutes shown as end of working time.

The third phase is the setting phase where the viscosity of the bone replacement material increases during the polymerization reaction, resulting in a hard cement. Once the cement is hardened, the practitioner can proceed to the next stage in the operation with reduced fear that the bone replacement material will move away from the implant area as it has now hardened. In FIG. 1, the temperature of the bone replacement material has increased at a steadily increasing rate, reaching a maximum of about 86° C. after about 9 minutes indicated by setting time). The maximum temperature of the bone replacement material is attained at about the end of the period over which the bone replacement material sets so that, at the end of the period, the bone replacement material will not move from the implant area.

Changing the conditions of the storage container for the bone replacement material and changing environmental factors such as the room temperature and humidity can affect the different phases. For example, changing the temperature of the components of the bone replacement material may lengthen the working time or dough phase to allow the practitioner to control the amount of time that is needed to implant the bone replacement material. Changing the temperature may also decrease the viscosity of the bone replacement material allowing easier delivery.

Changing room temperature by 10° C., for example, may decrease the time to set by a factor of 1.5 to 2. Because it is often difficult for a practitioner to control the temperature of the operating room, the monomer, the powder, and the mixing vessels may be cooled. The Table 1 below lists some bone replacement material working times and temperatures of the mixing components.

TABLE 1

Cement Working Times

| Cement Type & Manufacturer | | 25° C. | 23° C. | 17° |
|---|---|---|---|---|
| CMW 1 (homopolymer) | Dough | 1.5 min. | 1.7 min. | 2.8 min. |
| Deputy Orthop. (Leeds, UK) | Set | 3.5 min. | 4.4 min. | 8 min. |
| Endurance (copolymer) | Dough | 2.5 min. | 1.7 min. | 2.8 min. |
| Deputy Orthop. (Leeds, UK) | Set | 4.5 min. | 4.4 min. | 8 min. |
| Osteobond (copolymer) | Dough | 3.6 min | 4.2 min. | 6.5 min. |
| Zimmer Orthop. (Warsaw, Ind.) | Set | 6 min. | 7.2 min. | 12 min. |
| Osteopal (copolymer) | Dough | 2.5 min. | 3.0 min. | 6.2 min. |
| Merck Biomaterial (Darmstadt, Germany) | Set | 4.5 min. | 5.1 min. | 10 min. |
| Palacos R (homopolymer) | Dough | 0.8 min. | 1.0 min. | 2.2 min. |
| Heraeus Kulzer GmbH & Co. (Wehrheim, Germany) | Set | 4.4 min. | 5.0 min. | 6.5 min. |
| Simplex P (copolymer) | Dough | 2.2 min. | 2.7 min. | 5.2 min. |
| Stryker Osteonics Howmedia | Set | 5.0 min. | 5.8 min. | 9 min. |
| Kyphon X ® HV-R ™ | Mixing | | 8.0 min. | |
| (Sunnyvale Ca) | Dough | | 8.0 min. | |
| | Set | | 4.0 min. | |

Dough = time from initial mix to cement no longer sticky
Set = time to cement firm Some bone replacement materials containing ceramic (e.g., calcium phosphate and/or magnesium) have a 0.5 to 2 minute dough time, a 2 to 8 minute working time and a 2 to 10 minute set time and the current device and methods can be utilized to monitor these times, as well as other times from available bone replacement products.

For some bone replacement materials, relative humidity<40% can prolong working times for 1-3 minutes. Conversely, humidity>60% can shorten working times by similar amounts. The current application allows the phases of the cure of the bone replacement material to be monitored and therefore, the guess work based on environmental factors and subjective experience can now be reduced or eliminated as the temperature of the bone replacement material and thus the viscosity and the time can be determined.

Figure 2:
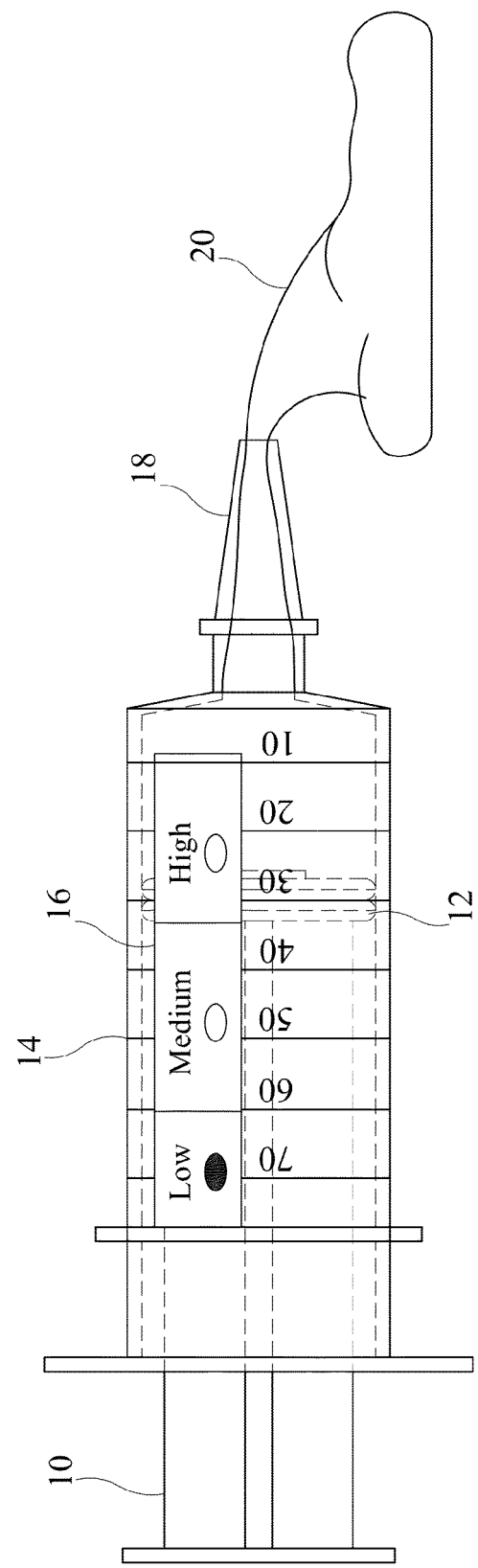
FIG. 2 is a perspective view of an embodiment of the mixed bone replacement material within the syringe being delivered. In or on the exterior of the syringe is a thermochromic material indicating temperature, viscosity and/or age of the bone replacement material.

FIG. 2 is a perspective view of an embodiment of the mixed bone replacement material 20 in the interior of the syringe, now being delivered from it. In or on the exterior 14 of the syringe is a thermochromic material 16 indicating temperature, viscosity and/or age of the bone replacement material. In the embodiment shown, the thermochromic material 16 is in or on the syringe barrel and the temperature is shown as low. The curing phases of the bone replacement material cause an exothermic reaction releasing heat, which is conducted to the syringe barrel. As the temperature increases in the interior of the syringe, the thermochromic material provides a visible indication of the temperature of the bone replacement material in the syringe barrel reaching a level which is characteristic of a phase in the cure by changing color, where the oval is changed to a solid color letting the user know that the cement is in the working phase.

The user can then push on second end of the plunger 10 and move or slide the first end of the plunger 12 in an upward direction or to a depressed position, which expels some or all of the bone replacement material 20 out of cannula or needle 18.

Shown in FIG. 2, the bone replacement material is not in direct contact with the exterior of the syringe so there is no need for the user to worry about the bone replacement material reacting with the thermochromic material, which may change the curing properties. Further, in the embodiment shown, the thermochromic material is not disposed in or on the cannula or needle 18. This will allow the user to deliver the bone replacement material without worry that the thermochromic material will come into contact and react with the bone replacement material. In some embodiments, the thermochromic material can be the same or different in different zones of the syringe barrel. In some embodiments, the thermochromic material can be present in the same or different quantities in one, two, three, four, five or more regions in or on the exterior of the syringe barrel. In this way, serial indicators can change color or generate a signal that allows the user to easily see which phase the bone replacement material is in.

In some embodiments, the thermochromic material can be part of the exterior of the syringe and made with it. The thermochromic material 16 may be part of the exterior of the syringe barrel or be affixed to the barrel, for example, by as a label, tape, film or strip using an attachment means such as an adhesive. Shown in FIG. 2 are three regions that the indicator has: low showing the color change from the thermochromic material, medium (no color change) and high (no color change). The amount of thermochromic material in each region, can be the same or different. For example, more thermochromic material can be in the medium and high indicators, where the color change or signal will be more apparent as the heat from the bone replacement material increases as the exothermic reaction continues and the heat is conducted through the syringe barrel causing a greater signal or color change of the thermochromic material in the other regions.

In some embodiments, the thermochromic material 16 may be incorporated into a carrier and applied to the exterior of the barrel or it may be added to the syringe and set in the exterior when the syringe is made. In some embodiments, the thermochromic material may be placed in a carrier (e.g., polymer) and applied to the label, tape or strip in some embodiments, the thermochromic material can be disposed in transparent material to make it easier to see.

In some embodiments, there may be a residual amount of bone replacement material remaining in the syringe after movement of the plunger and delivery to the implant site. This residual amount can therefore be able to indicate the extent of cure throughout the subsequent period in which the bone replacement material is curing in the implant site. The user can now look at the syringe and identify which phase the cement is at in vivo at the implant site.

Now that the temperature of the bone replacement material is known, the thermochromic material can be calibrated to determine the viscosity and or time of the bone replacement material and as the thermochromic material changes color because of increases in temperature, the change to the user can be visible and indicated as viscosity on the exterior of the syringe (e.g., low viscosity (17° C.), medium viscosity (27° C.), high viscosity (52° C.)). Therefore, depending on the type of bone replacement material, the thermochromic material can be calibrated to give a viscosity indication based on the temperature. As the temperature from the polymerization reaction increases, the viscosity will increase. Therefore, the user can now know directly the temperature of the bone replacement material. The user can also know indirectly the viscosity of the bone replacement material and the indicator can be configured to show this.

For example, during the working phase, in some embodiments, there are two requirements for bone replacement material viscosity—it should be sufficiently low to facilitate the delivery of the dough or paste from the syringe to the bone site, and it should penetrate into the interstices of the trabecular bone. On the other hand, the viscosity of the bone replacement material should be sufficiently high to withstand the back bleeding pressure, thus avoiding the risk of inclusion of blood into the bone replacement material, because this could significantly reduce the stability of the bone material.

By monitoring temperature, the viscosity can be shown in the indicator as well and the user will know the stage of the working time that they are in and if the viscosity has increased so much that the bone replacement material has hardened in the syringe or is too viscous to deliver.

Similarly, the thermochromic material can be configured in the indicator to show age of the bone replacement material. As the polymerization reaction and curing occurs, time and age of the bone replacement material increases with the temperature. By monitoring temperature, the time or phase of the bone replacement material can be shown in the indicator as well and the user will know the stage of the working time that they are in and if the time or age of the bone replacement material has increased so much in the syringe that the bone replacement material has hardened in the syringe or is too viscous to deliver.

Figure 3:
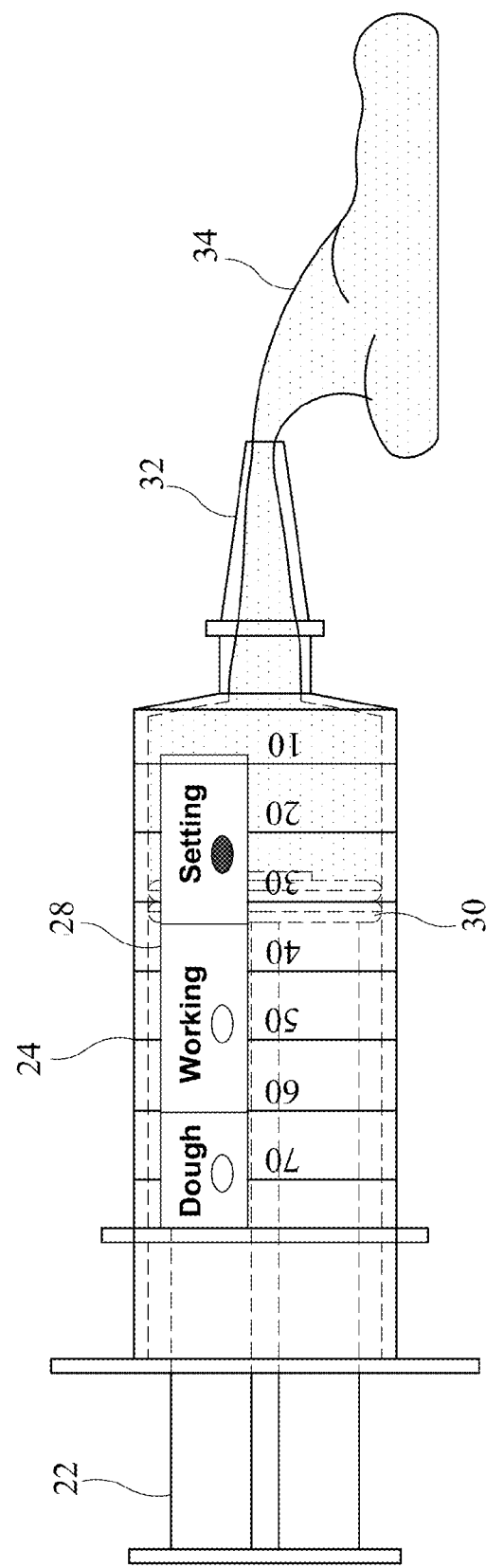
FIG. 3 is a perspective view of an embodiment of the mixed bone replacement material within the syringe being delivered. On the exterior of the syringe is a time indicating label, which shows the phase of the bone replacement material.

FIG. 3 is a perspective view of an embodiment of the mixed bone replacement material 34 within the syringe being delivered. In this view, the user pushed on the second end of the plunger 22 and moved or slid the first end of the plunger 30 in an upward direction or to a depressed position, which expels some or all of the bone replacement material 34 out of cannula or needle 32. On the exterior 28 of the syringe is a time indicating label 24, which shows the time and state of the bone replacement material (e.g., dough time, working time, setting time). In this view, the setting time is indicated and the user will know that the bone replacement material should not be delivered and is hardening at the site that it was delivered to.

The components of the device (e.g., syringe, plunger, cannula, or needle) may be made from materials, such as for example, polyurethane, polyurea, polyether(amide), PEBA, thermoplastic elastomeric olefin, copolyester, and styrenic thermoplastic elastomer, polypropylene, nylon, rubber, steel, aluminum, stainless steel, titanium, metal alloys with high non-ferrous metal content and a low relative proportion of iron, carbon fiber, glass fiber, plastics, ceramics or combinations thereof. The components can be the same or different colors or can be transparent or combinations thereof. The components may optionally include one or more tapered regions. The components will desirably be unaffected by contact with the bone replacement material and/or sterilizable by gamma radiation.

The cannula or needle 32 can be attached to the syringe by a leur fitting or snap fit. In some embodiments, the cannula or needle may optionally include one or more tapered regions. In some embodiments, the cannula or needle may be beveled. The cannula or needle may also have a tip style vital for accurate application based on the anatomic site for delivering the bone replacement material. Examples of tip styles include, for example, blunt tips, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle of the device may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of application. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In some embodiments, the bone replacement material delivery device is constructed for single use and/or is disposable. The bone replacement material delivery device can be relatively inexpensive and easy to use.

Thermochromic Material

The thermochromic material can provide an indication of the extent of cure of a bone replacement material. The indication will involve a change in the color or the addition of color to the exterior of the syringe, which is caused by exposure of the interior of the syringe to a change in temperature of the bone replacement material as it cures. This temperature change will be conducted through the syringe to the exterior of it and cause the thermochromic material to change color, become colorless, or add color. The thermochromic material can be selected to indicate a color change or addition when the temperature of the bone replacement material is characteristic of, for example, the beginning of the working time, or the end of it or the beginning of the setting time. A plurality of different thermochromic materials can be used to indicate temperatures which are characteristic of different stages in the cure of a cement material.

Thermochromic materials which can be used in the exterior of the device, label, strip, film, and/or tape can change between two colors, or between a colored condition and colorless condition. A thermochromic material can have an activation temperature, which is the temperature at which the material has reached its final color (or clear) state. The color change can take place when the sensed temperature increases towards the activation temperature over a small range of temperatures extending from about 1, 2, 3, 4, or 5° C. below or above the activation temperature.

The device can include a second region and a third region that can indicate temperature change, which can be loaded with a second thermochromic and third thermochromic material. The first, second and third thermochromic materials can have different activation temperatures, for example to indicate different stages in the curing reaction of the bone replacement material. For example, the indicator may change color to indicate that the cement has cured sufficiently for it to be ready to be injected into the bone cavity. The indicator may change color, for example, to indicate that the bone replacement material has cured so much that it should not be worked any further. The indicator may change color, for example, to indicate that the cement has set.

The thermochromic material can be on or in the exterior of the device to enhance the visibility of the bone replacement material in the interior of the syringe. The syringe can be at least partially transparent (for example translucent). This can be useful for the user of the device to inspect for voids in the bone replacement material once it is in the interior of the syringe.

In the embodiments, where the thermochromic material is made with the exterior of the syringe barrel, the polymer or carrier loaded with the thermochromic material is used to form the syringe barrel by a molding process (a process which involves the application of heat and pressure).

In some embodiments, the thermochromic material can be provided in a separate piece which can be placed on the exterior of portions or all of the syringe in appropriate intimate contact with the exterior so that a change in the temperature of the exterior of the syringe can be sensed by the thermochromic material. The thermochromic material can be fastened to the exterior of the syringe, for example, by means of a bonding material, such as for example, an adhesive or mechanically, for example by means of pins or screws. In some embodiments, the thermochromic material can be disposed around the circumference of all or portions of the exterior of the syringe.

Some polymers that can be a carrier for the thermochromic material include, but are not limited to, polyolefins, polyamides, polyesters, ethylene polymers, propylene polymers, or the like.

Thermochromic material that can be used in the current application can be any material that changes color in response to temperature. Thermochromic material includes, but is not limited to, a thermochromic dye material which is encapsulated in a polymeric carrier. For example, a thermochromic material can be provided in the form of microcapsules which contain crystal violet lactone, a weak acid, and a dissociable salt dissolved in a non-polar or slightly polar solvent liquid crystal solvent such as dodecanol or another suitable liquid crystal solvent. When the mixture is a solid, the dye exists in its lactone leuco form. However, when the liquid crystal solvent melts, the salt dissociates, the pH inside the microcapsule lowers (making protons readily available), the dye becomes protonated, and the lactone ring opens causing its absorption spectrum to shift, absorbing in the visible spectrum, such as a deeply violet color for crystal violet lactone. Suitable thermochromic dyes can be based on mixtures of leucodyes with suitable other chemicals, which display a color change (usually between a colorless leuco form and the colored form of the dye) dependent on the temperature.

Thermochromic materials which can be used in the current application also include, but are not limited to, spirolactones, fluorans, spiropyrans, or fulgides. Weak acids that can be used as proton donors include bisphenol A, parabens, 1,2,3-triazole derivatives, and 4-hydroxycoumarin. These weak acids can function as a proton donor to cause a dye molecule to change between its leuco form and its protonated colored form. Stronger Bronsted acids (better proton donors) can also be used but they tend to make the color change irreversible. Other thermosensitive dyes that can be used include an oxazine-based leuco thermosensitive dye (such as that sold under the trade mark CSB-12 by Hodogaya Chemicals Co), a spiropyran-based leuco thermosensitive dye (such as that sold under the trade mark CSR-13 by Hodogaya Chemicals Co), a quinoline-based thermosensitive dye (such as that sold under the trade mark CSY-13 by Hodogaya Chemicals Co) or the like.

Specific thermosensitive dyes that can be used in the thermochromic material are non-toxic and are known to activate at temperatures in the range of 21 to 51° C. and which are available from SICPA Securink Corporation of Springfield, Va. These dyes include 744020TC (thermochromic blue), 744010TC (thermochromic turquoise), 744027TC (thermochromic yellow), 734010TC (thermochromic rose), 724010TC (thermochromic orange), 754027TC (thermochromic green). There are also thermochromic dyes which lose color when heated, so that they change from a color towards clear. These dyes include 178002TC (black/clear) which is active at 27 to 36° C. Compounds which are active at 22 to 31° C. include 128001TC (orange/clear), 1384175TC (rose/clear), 150015TC (green/clear), 148003TC (blue/clear), 17800TC (black/clear), 14001TCBR (blue/red) or 128001TCY (orange/yellow). Compounds which are active from 23 to 33° C. include 118000TC (yellow/clear), 128002TC (orange/clear), 138103TC (vermillion/clear), 15002TC (green/clear), 14001TC (blue/clear), 14000TCBR (blue/red) and 128001TCY (orange/yellow). Compounds which are active at 23 to 33° C. include 11800TC (yellow/clear), 128002TC (orange/clear), 138103TC (vermillion/clear), 15002TC (green/clear), 14001TC (blue/clear), 14000TCBR (blue/red) and 128002TC (orange/yellow). Compounds which are active at 32 to 41° C. include 13001TC (rose/clear), 148002TC (blue/clear), 178001TC (black/clear) or 178002TCBR (blue/red). The compound should be non-toxic. In one embodiment, the thermochromic material is available from B&H Colour Change Limited of London GB-SW18 2RU.

In some embodiments, the thermochromic material can comprise bacteria. These bacteria start metabolic processes at certain temperatures and release chemicals that could interact with a substrate causing a color change. Some bacteria (e.g., *Rhodospirillum rubrum*) will change color in response to temperature because they have chromatophores in their membrane. These types of bacteria can be used in the present application.

In some embodiments, the change in the color of the thermochromic material can be detected by visually inspecting the color change. In some embodiments, a spectrophotometer or some other optical sensor instrument can be used to detect the color change to provide greater precision, or to differentiate between small changes in color. Using an optical sensor that can detect color change allows one to find the optimum extent of cure when tints of various colors are detected (e.g., small changes on the pantone scale). The concentration of the thermochromic material will be selected to provide an adequately visible color change response.

Figure 4A:
FIG. 4a is a schematic cross-sectional view of an embodiment of the time indicating label having first and second surface before it is activated.

FIG. 4a is a schematic cross-sectional view of an embodiment of the time indicating label. The time indicator label 40 comprises a first surface 38 having an acid-base indicator composition and a second surface 36 comprising an activator, wherein when the first surface 38 is brought into contact with the second surface 36 or when the second surface 36 is brought into contact with the first surface 38, at least a portion of the label changes color indicating elapsed time. The first surface 38 and the second surface 36 can have a pressure sensitive adhesive disposed on one or both surfaces so that when pressure is applied, the first and second surfaces adhere to each other and the chemical reaction is activated and the transfer of protons will cause color changes that can be visualized in the indicator 39 disposed on or in the first surface 38, second surface 36 or label 40.

The indicator allows easy viewing of the color change. As time passes and the reaction proceeds, the indicator changes color or, in some embodiments, becomes colorless. In this embodiment, time will proceed irrelevant of the temperature of the syringe. The time indicator label can have acid-base indicators and activators that cause color change over the minutes that represent the different phases from mixing time, dough time, working time, and/or setting time of the bone replacement material. In this way as time passes, the user will know from the color or lack of color which phase the bone replacement material is in. The label can be calibrated based on the bone replacement material being used.

Figure 4B:
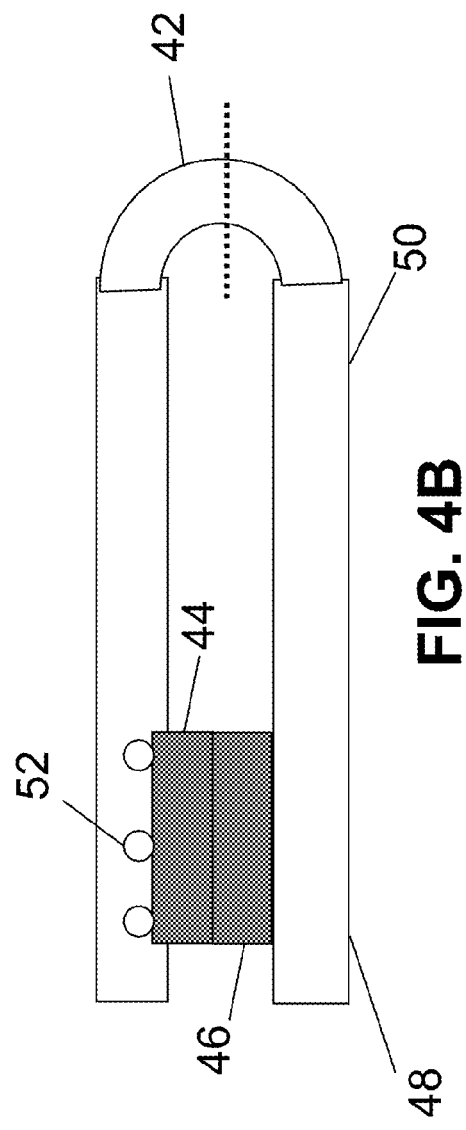
FIG. 4b is a schematic cross-sectional view of an embodiment of the time indicating label having first and second surface folded over to bring the acid-base indicator in the first surface in activating contact with the activator in the polymeric material of the second surface, which will produce time indicating signal.

FIG. 4b is a schematic cross-sectional view of an embodiment of the time indicating label. The time indicator label 48 comprises a first surface 44 having an acid-base indicator and a second surface 46 comprising an activator, wherein when the first surface 44 is brought into contact with the second surface 46 or when the second surface 46 is brought into contact with the first surface 44, at least a portion of the label changes color indicating elapsed time. The first surface 44 and the second surface 46 can have a pressure sensitive adhesive disposed on one or both surfaces so that when pressure is applied the surfaces adhere to each other. The chemical reaction is activated and the transfer of protons will cause color changes that can be visualized in the indicator 52 disposed on or in the first surface 44, second surface 46 or label 48.

In the embodiment shown in FIG. 4b, the acid-base indicator in the first surface 44 is brought into activating contact with the activator in the second surface 46 by folding the label along folding axis indicated by 42 such that the time indicating label is activated and a color change or color loss will occur in the indicator 52. The indicator allows easy viewing of the color change or color loss.

In some embodiments, the label 48 has an adhesive, strip, or film 50 disposed on it. When the user activates the label by applying pressure to the first and second surfaces or by folding the label so that first and second surfaces contact each other, this will activate the time indicating label. The user can now place the adhesive part on the syringe barrel and the label will be a "time keeper" for the bone replacement material. All the user need do is look at the syringe exterior to determine the phase the bone replacement material is in. As time occurs and the reaction proceeds, the indicator, changes color or, in some embodiments, become colorless. Time will proceed irrelevant of the temperature of the syringe. The time indicator label can have acid-base indicators and activators that cause color change over the minutes that represent the different phases from mixing time, dough time, working time, and/or setting time. In this way as the color changes, the user will know from the color or lack of color which phase the bone replacement material is in.

Label

The time indicator has a label having first and second surfaces. The label may be clear, or opaque. The label is flexible enough to bend and have the acid-base indicator composition come into contact with the activator composition. In one embodiment, the color change is visible through the label. In one embodiment, the label is substantially transparent. That is, the color change can be observed through the label. In one embodiment, the label is clear, colorless and completely transparent. The label may have one or more coatings to improve thermochromic material adhesion and/or ink adhesion.

The label may be any sheet or film capable of bending as described above. In one embodiment, the label may be any film intended for use as label face stock or tape. This label can be a polymer film, paper sheet, or combination thereof. The color change in the acid-base indicator caused by the activator can be observed through the label. When used as a label, the face side may have a printed or a printable surface. This label can be a single-layered sheet or polymer film or it can be a multi-layered construction. The multi-layered constructions and polymer films have two or more layers, or about two to about seven layers, or about three to about five layers. The layers of such multi-layered constructions and polymer films can have the same composition and/or size or they can be different. The label can have any thickness that is suitable for sheets or films intended for use as labels or tapes, with thicknesses in the range from about 500 microns to about 2 mm.

The polymer films include polyolefins (linear or branched), polyamides, polystyrenes, nylon, polyesters, polyester copolymers, polyurethanes, polysulfones, polyvinylidine chloride, styrene-maleic anhydride copolymers, styrene-acrylonitrile copolymers, ionomers based on sodium or zinc salts of ethylene methacrylic acid, polymethyl methacrylates, cellulosics, fluoroplastics, acrylic polymers and copolymers, polycarbonates, polyacrylonitriles, and ethylene-vinyl acetate copolymers. Included in this group are the acrylate copolymers such as ethylene methacrylic acid, ethylene methyl acrylate, ethylene acrylic acid and ethylene ethyl acrylate copolymers. Also, included in this group are polymers and copolymers of olefin monomers having from 2 to about 12, or from 2 to about 8 carbon atoms. These include the polymers of alpha-olefins having from 2 to about 4 carbon atoms per molecule. These include polyethylene, polypropylene, poly-1-butene, etc. An example of a copolymer within the above definition is a copolymer of ethylene with 1-butene having from about 1 to about 10 weight percent of the 1-butene comonomer incorporated into the copolymer molecule.

The polyethylenes that are useful for the label have various densities including low, medium and high density ranges. The low density range is from about 0.910 to about 0.925 g/cm$^3$; the medium density range is from about 0.925 to about 0.940 g/cm$^3$; and the high density range is from about 0.940 to about 0.965 g/cm$^3$. Films prepared from blends of copolymers or blends of copolymers with homopolymers also are useful.

In one embodiment, the label can be a polymer-coated paper which comprises a sheet of paper that is coated on either one or both sides with a polymer coating, so long as the label is substantially transparent. The polymer coating, which comprises a high, medium, or low density polyethylene, polypropylene, polyester, and other similar polymer films, is coated onto the label surface to add strength and/or dimensional stability. The weight of these types of coated paper labels can vary over a wide range with weights in the range of about 10 to about 50 lb/ream being useful. In total, the final coated paper label may comprise between about 10% and about 40% by weight polymer. For two-sided coatings, the quantity of polymer is approximately evenly divided between the top or face side and the bottom or underside of the paper.

Carriers

The label may have either an acid-base indicator composition or an activator composition on one or more of its surfaces. These compositions comprise an acid-base indicator compound or an activator compound and a carrier. The carriers are generally applied by coating or printing technologies, such as flexo printing. The carriers may include polymeric materials, inks, varnishes and/or pressure sensitive adhesives.

In one embodiment, the carrier may be an ink such as water-based, solvent-based or a radiation-curable ink appropriately chosen for the particular construction of the label. Specific examples of inks which can be utilized as a non-adhesive material include Sun Sheen (a product of Sun Chemical Company identified as an alcohol dilutable polyamide ink), Suntex MP (a product of Sun Chemical Company identified as a solvent-based ink formulated for surface printing acrylic coated substrates, PVIDC coated s and polyolefin films), X-CEL (a product of Water Ink Technologies identified as a water-based film ink for printing film substrates), Uvilith AR-109 Rubine Red (a product of Daw Ink identified as a UV ink) or CLA 91 598F (a product of Sun Chemical identified as a multibond black solvent-based ink). An example of a useful solvent based ink is No-Tox Liquid Ink FGN 41 21 and an example of a useful water based ink is No-Tox Liquid Ink FGN 3359, both of which are available from Colorcon, a division of Berwind Pharmaceutical Services, West Point, Pa.

In another embodiment, the carrier may be solvent-based or water-based varnish. The varnish may comprise one or more organic polymers or copolymers such as polyolefins, polyamides, polyesters, polyester copolymers, polyurethanes, polysulfones, polyvinylidene chloride, styrene-maleic anhydride copolymers, styrene-acrylonitrile copolymers, ionomers based on sodium or zinc salts of ethylene methacrylic acid, polymethyl methacrylates, acrylic polymers and copolymers, cellulosic polymers, acetate polymers, polyvinyl chlorides, polycarbonates, polyacrylonitriles, ethylene-vinyl acetate copolymers, and mixtures of two or more thereof dissolved or dispersed in a diluent. Examples of the diluents that can be used include alcohols such as ethanol, isopropanol butanol; esters such as ethyl acetate, propyl acetate, butyl acetate; toluene, xylene; ketones such as acetone, methyl ethyl ketone, mineral spirits and mixtures thereof. The ratio of polymer to diluent is dependent on the viscosity required for the application of the carrier, and the selection of such viscosity is within the skill of the art. Example of varnishes that can be used as carrier materials include CLBO 4275F-Prokote Primer (a product of Sun Chemical Corporation identified as a solvent based primer useful with inks and coatings). The carriers utilized typically have a thick coating weight of from about 1 to about 5 gsm (grams per square meter) or from about 1 to about 2 gsm.

In one embodiment, the varnish is a UV-curable varnish. Nonlimiting examples of UV-curable varnishes include Envirocure UV-1801, available from Environmental Ink and Coating Corp. (Morgantown, N.C.), and Clear Coating RCA 01291R, available from Sun Chemical (Rochester, N.Y.). An example of a clear UV-cured acrylic varnish currently available under the designation Flexographic UV Curable Varnish, UVF 02037, is available from Akzo Nobel Inks Corp., Langhorne, Pa. Envirocure UV-1801 is non-yellowing, offers good flexibility and resistance to cracking, provides rapid cure response, and provides good scuff resistance. Clear Coating RCA 01291 R is light- and temperature-stable and exhibits high gloss and lay, with excellent adhesion. The varnish can be applied as a liquid and then cured with ultraviolet light. In one embodiment, the varnish is applied at a coat weight (measured after drying) of from about 1 to about 5 gsm, or from about 2.5 to about 4.5 gsm. Alternatively, a thin layer (approximately 0.5 gsm) of silicone is used in place of the UV-curable varnish layer.

In some embodiments, the label contains a pressure sensitive adhesive. The pressure sensitive adhesive is present in an amount from about 5 to about 45, or from about 7 to about 30 or to about 9 to about 25 grams per square meter (gsm or g/m$^2$). In some embodiments, the pressure sensitive adhesive contains at least one acid-base indicator or at least one activator. In some embodiments, the acid-base indicator composition and the activator compound can be in different surfaces and in different layers.

The pressure sensitive adhesive may contain any pressure-sensitive material known in the art for making labels, tapes or the like. The pressure sensitive adhesive must be able to adhere to the first surface, second surface, label, or syringe. The adhesives include rubber based adhesives, acrylic adhesives, vinyl ether adhesives, silicone adhesives, and mixtures of two or more thereof. The pressure sensitive adhesive material that is useful may contain as a major constituent an adhesive polymer, such as acrylic-type polymers; block copolymers; natural, reclaimed, or styrene-butadiene rubbers; tackified natural or synthetic rubbers; or random copolymers of ethylene and vinyl acetate, ethylene-vinyl-acrylic terpolymers, polyisobutylene, poly(vinyl ether), etc. The pressure sensitive adhesives will exhibit good adhesion to the syringe.

Acid Base Indicators

The time-indicating label contains at least one acid-base indicator with or without a carrier. The acid-base indicator is generally present in an amount from about 0.01% to 10%, or from about 0.03% to about 7%, or from about 0.05% to about 5% by weight. In some embodiments, useful acid-base indicators are those which change color at a relatively low pH, upon exposure to an acid. The acid-base indicator should be one which produces a distinct color change, whether the color change is from one color to another or from colorless to colored, at the appropriate pH value.

In one embodiment, the acid-base indicator can change color at a pH less than about 4. In another embodiment, the acid-base indicator can change color at a pH less than about 3. In another embodiment, the acid-base indicator can change color at a pH less than about 2. In one embodiment, the acid-base indicator can change color at a pH of about 1.8 or less.

In one embodiment, the acid-base indicator can comprise bromophenol blue (3',3",5',5" tetrabromophenolsulfonephthalein). In another embodiment, the acid-base indicator can comprise cresol red (o-cresolsulfonephthalein). In another embodiment, the acid-base indicator can comprise metanil yellow (4'-aniline azobenzene-sulfonic acid, Na salt). Other useful acid-base indicators include Methyl Violet; Crystal Violet; Ethyl Violet; Malachite Green; Methyl Green; 2-(p-dimethylaminophenylazo)pyridine; Quinaldine Red; Paramethyl Red (p-(p-dimethylaminophenylazo)benzoic acid, Na salt); 4-phenylazodiphenylamine; Thymol Blue (thymolsulfonephthalein); Metacresol Purple (m-cresolsulfonephthalein); Orange IV (p-(p-anilinophenylazo(benzenesulfonic acid, Na salt); 4-o-tolylazo-o-toluidine; erythrosin, disodium salt; Benzopurpurine 48; N,N-dimethyl-p-(m-tolylazo) aniline; 4,4'-bis(2-amino-1-naphthylazo)2,2'-s-tilbene sulfonic acid; tetrabromophenolphthalein ethyl ester, K salt; p-dimethylaminoazobenzene; Methyl Orange (4'-dimethylaminoazobenzene-4-sulfonic acid, Na salt); or 2-(p-dimethylaminophenylazo)pyridine or a combination thereof.

Activators

The time-indicating label contains at least one activator composition with or without one or more of the above carriers. In one embodiment, the activator compound is an organic acid. Examples of organic acids include carboxylic acids, sulfonic acids, phosphoric acids, etc. The organic acids are those selected to migrate from the first or second surface to the acid-base indicator, which then produces a color change or color loss. The organic acids typically contain from 1 to about 40, or from about 4 to about 30, or from about 6 to about 24 carbon atoms. The acids cause the color change of the acid-base indicator. Specific organic acids which may be used include paratoluene sulphonic acid, naphthalene sulphonic acid and camphor sulphonic acid, oxalic acid, maleic acid, dichloroacetic acid, trichloroacetic acid, benzenesulfonic acid, chloroanilic acid, etc.

In one embodiment, the activator is an alkyl benzene sulfonic acid. In one embodiment, the alkyl group may be a straight-chain alkyl group or a branched-chain alkyl group. In one embodiment, the alkyl group may include from about 1 to about 30, or from about 3 to about 18, or from about 6 to about 12 carbon atoms. The alkyl group may be substituted or un-substituted. If substituted, it may be substituted with a group which does not change the substantially hydrocarbyl nature of the alkyl group. Such substituents include, for example, halogen atoms and aromatic moieties. Illustrative alkyl radicals include isopropyl, isobutyl, n-butyl, sec-butyl, the isomeric amyl radicals, the isomeric hexyl radicals, the isomeric heptyl radicals and the isomeric octyl radicals. Illustrative alkylphenyl radicals include butylphenyl, amylphenyl, diamylphenyl, octyl-phenyl, etc. Other substantially hydrocarbon radicals are useful such as tetradecyl, octadecyl, eicosyl, butylnaphthyl, hexylnaphthyl, octylnaphthyl, naphthenyl, etc. If substituted with halogen atoms, the alkyl group may be substituted with single or multiple halogen atoms. The halogen atoms include fluorine, chlorine, bromine and iodine.

The activator may be present in either a pressure sensitive adhesive or in an ink or varnish or other polymeric material layer of the label. The activator may be present at a suitable concentration, depending on the rate at which the activator diffuses, the strength of color change desired, and the nature of the activator itself. In one embodiment, the activator is present at a concentration in a range from about 1 wt % to about 10 wt %, in one embodiment from about 2 wt % to about 8 wt % and in one embodiment, at about 6 wt %.

In one embodiment, the time indicating label further comprises a peelable liner that covers the first and second surfaces, label and/or adhesives. To activate the time indicating label, the user removes the peelable liner to expose the surfaces to be brought into contact with each other. In some embodiments, the label has an adhesive, when the peelable liner is removed from it, the label now can be attached to the surface of the syringe.

As described above, the label may be manipulated, such as by folding or bending the label, to bring at least a portion of the first surface into activating contact with at least a portion of the second surface. Activating contact may be direct contact or contact through one or more additional layers, such as the barrier layer or a time delay or diffusion-delay layer. After the time indicating label has been activated and attached to a syringe loaded with bone replacement material, the label may be monitored. Since the color change is visible through the label, the label may be monitored simply by observing the label during routine handling of the syringe to which the label is attached.

The activator migrates from the first or second surface and comes into contact with the acid-base indicator, the acid-base indicator then changes color. The color change may be from colorless to colored, or may be from a first color to a second color. In either case, the color which is newly formed should be strong enough to be easily observable through the label. Of course, the label should be sufficiently transparent that the color can be observed through the label.

Thus, in one embodiment, the activator compound is capable of migrating at a rate which is temperature-dependent from the polymeric material into the acid-base indicator. In one embodiment, at a given temperature, the rate of migration is determined by the components of the surface.

In one embodiment, the rate of migration of the activator depends on the nature of the polymer in the first surface. In another embodiment, the rate of migration depends also on the nature of the second surface. Thus, by judicious selection of the materials in the first and second surfaces, the acid-base indicator and the activator, the rate of migration can be controlled and adjusted to the specific type of bone replacement material used. This can be calibrated to the different phases of the bone replacement material (e.g., dough time, working time, setting time, waiting time, etc.).

In another embodiment, the rate of color change at a given temperature is a function of the concentration of the acid-base indicator and activator. Thus, by increasing the concentration of the acid-base indicator and/or activator, the time for color development can be extended. In another embodiment, the rate of color change at a given temperature is a function of the coating weight of the first and second surfaces. Thus, by increasing the quantity of the acid-base indicator and by increasing the coating weight of the first surface, the time for color development can be extended.

In yet another embodiment, there is a method of monitoring curing of mixed bone replacement material, the method comprising providing a syringe having an exterior, and an interior having mixed bone replacement material therein, the syringe comprising a plunger slidable within the interior of the syringe, the plunger having a first end and a second end, the second end configured for moving the first end of the plunger to at least a depressed position to displace mixed bone replacement material from the syringe; and monitoring (i) a thermochromic material disposed in or on the exterior of the syringe, the thermochromic material configured to provide an indication of temperature, viscosity, and/or age of bone replacement material in the interior of the syringe or (ii) a time indicating label disposed on the exterior of the syringe, the time indicating label having a first surface comprising an acid-base indicator composition and a second surface comprising an activator, wherein when the first surface is brought into contact with the second surface or when the second surface is brought into contact with the first surface, at least a portion of the label changes color indicating elapsed time, thereby monitoring the curing of mixed bone replacement material.

In one embodiment, there is a method of monitoring curing of mixed bone replacement material, where the thermochromic material or time indicating label are monitored for color change indicating that the mixed bone replacement material has reached a pre-determined temperature or viscosity, which is the mixing, doughy, working, waiting, and/or setting phase.

In one embodiment, there is a method of monitoring curing of mixed bone replacement material, where the thermochromic material or time indicating label have a thickness of about 500 µm to about 2 mm.

Bone Replacement Material

Bone replacement materials can include bone particles from fully mineralized bone, and demineralized bone particles and combinations thereof. The bone particles can be autograft, allograft, xenogenic, transgenic bone particles or a combination thereof.

In some embodiments, the bone replacement material includes bone cements. Bone cements are commonly provided in two or more components. The first component is usually a powder and the second component is usually in liquid form. Examples of bone cement materials include those based on acrylate materials which can react by polymerization to form acrylate polymers. Typically, a bone cement can be formed by mixing a liquid acrylate monomer with a powder such as acrylate polymer using a mixing element, where the mixing can be accomplished by hand or machine. The resulting mixture has a paste or dough-like consistency. Typically, the components of the mixture react, involving polymerization of the acrylate monomer and copolymerization with the acrylate polymer particles. The viscosity of the cement composition increases during the reaction, resulting in a hard cement. The curing reaction of a bone cement material is generally exothermic.

In some embodiments, the bone cement comprises powder that includes, for example, calcium phosphate based powders and poly-methyl-methacrylate based powders. Any of various osteoconductive powders, such as ceramics, calcium sulfate or calcium phosphate compounds, hydroxyapatite, deproteinized bone, corals, and certain polymers, can alternatively or additionally be used in the bone cement.

Typically, the bone cement is prepared prior to injection by mixing bone-cement powder (e.g., poly-methyl-methacrylate (PMMA)), a liquid monomer (e.g., methyl-methacrylate monomer (MMA)), an x-ray contrast agent (e.g., barium sulfate), and an activator of the polymerization reaction (e.g., N,N-dimethyl-p-toluidine) to form a fluid mixture. Other additives including but not limited to stabilizers, drugs, fillers, dyes and fibers may also be included in the bone cement. Since the components react upon mixing, immediately leading to the polymerization, the components of bone cement should be kept separate from each other until the user is ready to form the desired bone cement. Once mixed, the user must work very quickly because the bone cement sets and hardens rapidly.

Other examples of bone cement compositions and/or their uses are discussed in US Patent Publication No. 20080109003, U.S. Pat. No. 7,138,442; U.S. Pat. No. 7,160,932; U.S. Pat. No. 7,014,633; U.S. Pat. No. 6,752,863; U.S. Pat. No. 6,020,396; U.S. Pat. No. 5,902,839; U.S. Pat. No. 4,910,259; U.S. Pat. No. 5,276,070; U.S. Pat. No. 5,795,922; U.S. Pat. No. 5,650,108; U.S. Pat. No. 6,984,063; U.S. Pat. No. 4,588,583; U.S. Pat. No. 4,902,728; U.S. Pat. No. 5,797,873; U.S. Pat. No. 6,160,033; and EP 0 701 824, the disclosures of which are herein incorporated by reference.

In some embodiments, other additives can be mixed with the bone cement and this includes bioactive substances. Thus, one or more bioactive substances can be combined with the bone cement by soaking or immersing the bone cement in a solution or dispersion of the desired bioactive substance(s). Bioactive substances include physiologically or pharmacologically active substances that act locally or systemically in the host. In certain applications, the bone cement can be used as a time-release drug delivery device for drugs or other bioactive substances that are to be delivered to the surgical site.

Bioactive substances which can be readily combined with the bone cement include, e.g., collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin or gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents or polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); osteoinductive factor; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; or nucleic acids. When employed, the total amount of bioactive substance can represent from about 0.1 to about 60 weight percent of the osteoimplant.

In some embodiments, the bioactive agent is mixed before, with or after the bone cement is added to the container. In some embodiments, the bioactive agent comprises the family of proteins known as the transforming growth factor-beta (TGFβ) superfamily of proteins, which includes the activins, inhibins, or bone morphogenetic proteins (BMPs). In some embodiments, the active agent includes at least one protein from the subclass of proteins known generally as BMPs. BMPs have been shown to possess a wide range of growth and differentiation activities, including induction of the growth and differentiation of bone, connective, kidney, heart, and neuronal tissues. See, for example, descriptions of BMPs in the following publications: BMP-2, BMP-3, BMP-4, BMP-5, BMP-6, and BMP-7 (disclosed, for example, in U.S. Pat. Nos. 5,013,649 (BMP-2 and BMP-4); 5,116,738 (BMP-3); 5,106,748 (BMP-5); 5,187,076 (BMP-6); and 5,141,905 (BMP-7)); BMP-8 (disclosed in PCT WO 91/18098); BMP-9 (disclosed in PCT WO 93/00432); BMP-10 (disclosed in PCT WO 94/26893); BMP-11 (disclosed in PCT WO 94/26892); BMP-12 or BMP-13 (disclosed in PCTWO 95/16035); BMP-15 (disclosed in U.S. Pat. No. 5,635,372); BMP-16 (disclosed in U.S. Pat. No. 6,331,612); MP52/GDF-5 (disclosed in PCT WO 93/16099); or BMP-17 or BMP-18 (disclosed in U.S. Pat. No. 6,027,917). The entire disclosure of these references is herein incorporated by reference. Other TGF-proteins that may be useful as the active agent of the bone cement paste include Vgr-2 and any of the growth and differentiation factors (GDFs), such as, for example, GDF-5.

A subset of BMPs that may be used in certain embodiments includes BMP-2, BMP-4, BMP-5, BMP-6, BMP-7, BMP-8, BMP-9, BMP-10, BMP-11, BMP-12 or BMP-13. In some embodiments, the composition contains two or more active agents (e.g., BMP-2 and BMP-4). Other BMPs and TGF-proteins may also be used.

The active agent may be recombinantly produced, or purified from another source. The active agent, if a TGFβ protein such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β (e.g., a heterodimer composed of one monomer each of a BMP and a related member of the TGF-β superfamily). Examples of such heterodimeric proteins are described, for example in published PCT Patent Application WO 93/09229.

In some embodiments, the amount of growth factor, (e.g., bone morphogenic protein) may be sufficient to cause bone growth. In some embodiments, the growth factor is rhBMP-2 and is contained in the bone replacement material in an amount of from 1 to 2 mg per cubic centimeter of the bone replacement material. In some embodiments, the amount of rhBMP-2 morphogenic protein is from 2.0 to 2.5 mg per cubic centimeter (cc) of the bone replacement material.

In some embodiments, the growth factor is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

The bone replacement material may be mixed with additional therapeutic agents. Exemplary therapeutic agents include but are not limited to IL-1 inhibitors, such as Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, or analgesic agent. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+) R and (−)—S enantiomers of the statin. In various embodiments, the statin may comprise a 1:1 racemic mixture of the statin.

One method of making the bone replacement material includes adding the powder to the container and adding the liquid and other components to the container and mixing them with a mixing element. The mixing element can be placed in the upper opening of the container and the mixing element stirred by hand or machine until the desired consistency of the slurry or paste or liquid is reached. Optionally, the mixture can include one or more other optional components such as any of binders, fillers, plasticizers, biostatic/biocidal agents, surface active agents, bioactive substances, or reinforcing components. The syringe is then filled with the bone replacement material and the thermochromic material is disposed on the exterior of the syringe and/or the time indicating label is placed on the exterior of the syringe and activated. The bone replacement material's phases are monitored by observing the color changes or color loss on the exterior. If appropriate, then the bone replacement material is then delivered to the anatomic site.

The bone replacement material can be injected at the desired anatomic site, for example, a hard tissue repair site, e.g., one resulting from injury, defect brought about during the course of surgery, infection, malignancy or developmental malformation, or the like. The bone replacement material can be utilized in a wide variety of orthopedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, sinus lifts, etc. Specific bones which can be repaired or replaced with the osteoimplant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal or metatarsal bones.

In some embodiments, the bone replacement material comprises two separate components, one component being liquid and a second component being solid and the bone replacement material is mixed with the top opening while being exposed to room air.

Kits

One or more of the devices' components may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment. In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the delivery device may be packaged in a moisture resistant package and then terminally sterilized by gamma irradiation. In use the practitioner removes the one or all components from the sterile package for use. In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize delivery device and/or one or more of its components (e.g., bone replacement material), including, but not limited to, gas sterilization, such as, for example, with ethylene oxide or steam sterilization.

In various embodiments, a kit is provided comprising sterile or non-sterile bone replacement material and/or diluents. The kit may include additional parts along with the delivery device combined together to be used with it (e.g., wipes, needles, syringes, etc.). The kit may include gloves, drapes, wound dressings and other procedural supplies for maintaining sterility of the delivery process, as well as an instruction booklet, DVDs, or CDs, which may include a chart that shows how to mix and use the device.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A bone replacement material delivery device, comprising: a syringe having an exterior, and an interior configured to receive bone replacement material, the syringe comprising a plunger slidable within the interior of the syringe, the plunger having a first end and a second end, the second end configured for moving the first end of the plunger to at least a depressed position to displace bone replacement material from the syringe; and a thermo chromic material disposed on a syringe barrel on the exterior of the syringe, the thermochromic material including a time indicating label displaying the time and state of bone replacement material in the interior of the syringe, the time and state of the bone replacement material comprising a dough time label, a working time label and a setting time label.

2. A bone replacement material delivery device according to claim 1, wherein (i) the thermochromic material is in a label disposed on the syringe barrel on the exterior of the syringe and the thermochromic material is in direct contact with the syringe and not in direct contact with the bone replacement material or (ii) the thermochromic material is on at least a portion of the syringe barrel and the exterior of the syringe is transparent so that the thermochromic material is visible to the user and the thermochromic material is not in direct contact with the bone replacement material.

3. A bone replacement material delivery device according to claim 1, wherein the thermochromic material is disposed in different quantities in a first region, a second region and a third region on the syringe barrel.

4. A bone replacement material delivery device according to claim 1, wherein the indication is provided along at least part of the exterior of the syringe on the syringe barrel.

5. A bone replacement material delivery device according to claim 1, wherein the thermochromic material is disposed in a polymer.

6. A bone replacement material delivery device according to claim 5, wherein the polymer comprises a polyolefin.

7. A bone replacement material delivery device according to claim 1, wherein the thermochromic material provides an indication of a temperature of the bone replacement material.

8. A bone replacement material delivery device according to claim 1, wherein the thermochromic material provides an indication of a viscosity of the bone replacement material.

9. A bone replacement material delivery device, comprising: a syringe having an exterior, and an interior configured to receive bone replacement material, the syringe comprising a plunger slidable within the interior of the syringe, the plunger having a first end and a second end, the second end configured for moving the first end of the plunger to at least a depressed position to displace any bone replacement material from the syringe; and a first time indicating label disposed on the exterior of the syringe on a syringe barrel, the first time indicating label having a first surface comprising an acid-base indicator and a second surface comprising an activator, wherein when the first surface is brought into contact with the second surface or when the second surface is brought into contact with the first surface, at least a portion of the label changes color indicating elapsed time and a thermochromic material that is disposed on the syringe barrel, the thermochromic material including a second time indicating label displaying the time and state of the bone replacement material in the interior of the syringe, the time and state of the bone replacement material comprising a dough time label, a working time label and a setting time label.

10. A bone replacement material delivery device according to claim 9, wherein the indication is provided along at least part of the exterior of the syringe on the syringe barrel.

11. A bone replacement material delivery device according to claim 9, wherein the first time indicating label also provides an indication of a temperature and/or viscosity of the bone replacement material.

12. A bone replacement material delivery device according to claim 9, wherein the first and second surfaces of the time indicating label remain adhered when brought into contact indicating elapsed time.

13. A bone replacement material delivery device according to claim 9, wherein the acid-base indicator changes color at a pH of about 1.8 or less.

14. A bone replacement material delivery device according to claim 9, wherein the acid-base indicator composition and the activator are in a carrier comprising a pressure sensitive adhesive, an ink or a varnish.

15. A bone replacement material delivery device according to claim 1, wherein the thermochromic material comprises bacteria.

16. A bone replacement material delivery device according to claim 9, wherein the acid-base indicator composition and the activator are covered by a peelable liner.

17. A bone replacement material delivery device according to claim 9, wherein the thermochromic material comprises bacteria.

* * * * *